United States Patent
Han et al.

(10) Patent No.: US 11,040,335 B2
(45) Date of Patent: Jun. 22, 2021

(54) METHOD FOR MANUFACTURING ZINC FERRITE CATALYST AND ZINC FERRITE CATALYST MANUFACTURED THEREBY

(71) Applicant: LG CHEM, LTD., Seoul (KR)

(72) Inventors: Jun Kyu Han, Daejeon (KR); Dong Hyun Ko, Daejeon (KR); Kyong Yong Cha, Daejeon (KR); Sang Jin Han, Daejeon (KR); Sunhwan Hwang, Daejeon (KR); Seongmin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 78 days.

(21) Appl. No.: 16/480,977

(22) PCT Filed: Dec. 19, 2018

(86) PCT No.: PCT/KR2018/016201
§ 371 (c)(1),
(2) Date: Jul. 25, 2019

(87) PCT Pub. No.: WO2019/132392
PCT Pub. Date: Jul. 4, 2019

(65) Prior Publication Data
US 2020/0001279 A1 Jan. 2, 2020

(30) Foreign Application Priority Data
Dec. 26, 2017 (KR) .......................... 10-2017-0179588

(51) Int. Cl.
*B01J 23/80* (2006.01)
*B01J 37/03* (2006.01)
(Continued)

(52) U.S. Cl.
CPC ............... *B01J 23/80* (2013.01); *B01J 37/03* (2013.01); *B01J 37/08* (2013.01); *C07C 5/48* (2013.01); *C07C 11/167* (2013.01)

(58) Field of Classification Search
CPC .. B01J 23/80; B01J 37/03; B01J 37/08; C07C 5/48
See application file for complete search history.

(56) References Cited

U.S. PATENT DOCUMENTS 8,513,479 B2 * 8/2013 Chung .................. B01J 23/002
502/329
2010/0121123 A1 5/2010 Chung et al.
(Continued)

FOREIGN PATENT DOCUMENTS

KR 10-0847206 7/2008
KR 10-0950373 3/2010
(Continued)

OTHER PUBLICATIONS

Gaudon et al (Structural defects in AFe2O4 (A=Zn, Mg) spinels, Mater Res Bull. 44 (2009) 479-484). (Year: 2009).*
(Continued)

*Primary Examiner* — Sheng H Davis
*Assistant Examiner* — Michael Forrest
(74) *Attorney, Agent, or Firm* — Dentons US LLP (57) ABSTRACT

Provided is a method for producing a zinc ferrite catalyst, the method comprising: preparing a zinc precursor solution; preparing a ferrite precursor solution; obtaining a first precipitate by bringing the zinc precursor solution into contact with an alkaline solution; obtaining a second precipitate by adding the ferrite precursor solution to the first precipitate; and drying and firing the second precipitate after filtering the second precipitate.

8 Claims, 4 Drawing Sheets

(51) Int. Cl.
*B01J 37/08* (2006.01)
*C07C 5/48* (2006.01)
*C07C 11/167* (2006.01)

(56) References Cited

U.S. PATENT DOCUMENTS

| | | | |
|---|---|---|---|
| 2012/0059208 A1* | 3/2012 | Mamedov | B01J 37/03 585/625 |
| 2013/0209351 A1 | 8/2013 | Shin et al. | |
| 2016/0368839 A1 | 12/2016 | Hwang et al. | |
| 2018/0333702 A1 | 11/2018 | Suh et al. | |

FOREIGN PATENT DOCUMENTS

| | | |
|---|---|---|
| KR | 10-1570943 | 11/2015 |
| KR | 10-2015-0141879 | 12/2015 |
| KR | 10-2016-0053499 | 5/2016 |
| KR | 10-2017-0068351 | 6/2017 |
| WO | 2009/045002 | 4/2009 |
| WO | WO-2009045002 A1 * | 4/2009 ............... C07C 5/48 |

OTHER PUBLICATIONS

International Search Report and the Written Opinion of PCT/KR2018/016201, dated Mar. 27, 2019.
Toledo-Antonio et al., "Correlation between the magnetism of non-stoichiometric zinc ferrites and their catalytic activity for oxidative dehydrogenation of 1-butene," Applied Catalysis A: General 234: 137-144 (2002).
Ladole, "Preparation and Characterization of Spinel Zinc Ferrite ZnFe2O4," Int. J. Chem. Sci. 10(3): 1230-1234 (2012).

* cited by examiner

METHOD FOR MANUFACTURING ZINC FERRITE CATALYST AND ZINC FERRITE CATALYST MANUFACTURED THEREBY

CROSS-REFERENCE TO RELATED APPLICATIONS

This application is a National Stage Application of International Application No. PCT/KR2018/016201 filed on Dec. 19, 2018, which claims priority to and the benefit of Korean Patent Application No. 10-2017-0179588 filed in the Korean Intellectual Property Office on Dec. 26, 2017, the entire contents of which are incorporated herein by reference.

TECHNICAL FIELD

The present specification relates to a method for producing a zinc ferrite catalyst and a zinc ferrite catalyst produced thereby.

BACKGROUND ART 1,3-butadiene is an intermediate of petroleum chemical products, and the demand and value for the same have gradually increased. The 1,3-butadiene has been produced by using the naphtha cracking process, the direct dehydrogenation reaction of butene, the oxidative dehydrogenation reaction of butene, and the like.

However, since the naphtha cracking process consumes a lot of energy due to high reaction temperature, and is not a single process for producing only 1,3-butadiene, there is a problem in that other fundamental oil components in addition to 1,3-butadiene are produced in excess. Further, the direct dehydrogenation reaction of n-butene is thermodynamically adverse and requires high temperature and low pressure conditions for producing 1,3-butadiene at high yield as an endothermic reaction, and thus is not suitable as a commercialization process for producing 1,3-butadiene.

Meanwhile, the oxidative dehydrogenation reaction of butene is a reaction in which butene and oxygen react with each other in the presence of a metal oxide catalyst to produce 1,3-butadiene and water, and has a thermodynamically very favorable advantage because stable water is produced. Further, since the oxidative dehydrogenation reaction of butene is an exothermic reaction unlike the direct dehydrogenation reaction of butene, 1,3-butadiene may be obtained at high yield even at low reaction temperature as compared to the direct dehydrogenation reaction, and the oxidative dehydrogenation reaction of butene may become an effective single production process capable of satisfying the demand for 1,3-butadiene because an additional heat supply is not required.

The metal oxide catalyst is generally synthesized by a precipitation method, and the one-time amount of metal oxide catalyst produced is small due to technological and spatial limitations, so that the catalyst is produced by repeating the same process several times in order to satisfy a target amount. The catalysts thus produced after several processes may have different reactivity with the reactant depending on the production order, and the difference in reactivity of such a catalyst is directly related to the yield of the product (butadiene), so that studies to reduce the difference in reactivity of the catalyst have been continuously carried out.

DETAILED DESCRIPTION OF INVENTION

Technical Problem

The present specification provides a method for producing a zinc ferrite catalyst.

Technical Solution

An exemplary embodiment of the present specification provides a method for producing a zinc ferrite catalyst, the method comprising:
preparing a zinc precursor solution;
preparing a ferrite precursor solution;
obtaining a first precipitate by bringing the zinc precursor solution into contact with an aqueous basic solution;
obtaining a second precipitate by adding the ferrite precursor solution to the first precipitate; and
drying and firing the second precipitate after filtering the second precipitate.

An exemplary embodiment of the present specification provides a zinc ferrite catalyst produced by the above-described method for producing a zinc ferrite catalyst.

Further, an exemplary embodiment of the present specification provides a zinc ferrite catalyst in which a molar ratio (ferrite/zinc (Fe/$Zn^a$)) of ferrite to zinc is 1 to 2.5.

In addition, an exemplary embodiment of the present specification provides a method for producing butadiene, the method comprising:
preparing the above-described zinc ferrite catalyst; and
producing butadiene by using the zinc ferrite catalyst in an oxidative dehydrogenation reaction of butene.

Advantageous Effects

In a zinc ferrite catalyst produced by a method for producing the zinc ferrite catalyst according to an exemplary embodiment of the present specification, the $\alpha$-$Fe_2O_3$ phase is decreased and the activity of the catalyst is increased.

Accordingly, 1,3-butadiene can be obtained at high yield as compared to a zinc ferrite catalyst in the related art, which is used in the oxidative dehydrogenation of butene.

BEST MODE

Hereinafter, the present specification will be described in more detail.

In the present specification, the 'yield (%)' is defined as a value obtained by dividing the weight of 1,3-butadiene, which is a product of an oxidative dehydrogenation reaction, by the weight of butene which is a raw material. For example, the yield can be represented by the following equation.

Yield (%)=[(the number of moles of 1,3-butadiene produced)/(the number of moles of butene supplied)]×100

In the present specification, the 'conversion (%)' refers to an amount of reactant converted into a product, and for example, the conversion of butene can be defined by the following equation.

Conversion (%)=[(the number of moles of butene reacted)/(the number of moles of butene supplied)]×100

In the present specification, the 'selectivity (%)' is defined as a value obtained by dividing the change amount of butadiene (BD) by the change amount of butene (BE). For example, the selectivity can be represented by the following equation.

Selectivity (%)=[(the number of moles of 1,3-butadiene or COx produced)/(the number of moles of butene reacted)]×100

An exemplary embodiment of the present specification provides a method for producing a zinc ferrite catalyst, the method comprising: preparing a zinc precursor solution; preparing a ferrite precursor solution; obtaining a first precipitate by bringing the zinc precursor solution into contact with an aqueous basic solution; obtaining a second precipitate by adding the ferrite precursor solution to the first precipitate; and drying and firing the second precipitate after filtering the second precipitate.

It is known that the activity of a ferrite-based catalyst having a spinel structure ($AFe_2O_4$) is good as a catalyst for a process of producing 1,3-butadiene through the oxidative dehydrogenation reaction of butene.

Meanwhile, it is known that a ferrite-based catalyst exhibits a result that is better than a bismuth-molybdenum catalyst (Mo—Bi catalyst) in terms of reactivity with 2-butene, particularly, trans-2-butene. Accordingly, even though the Mo—Bi catalyst is applied to the oxidative dehydrogenation reaction of 2-butene, an effect which is the same as that in the present invention, that is, a result such as the conversion of butene or selectivity of butadiene is not obtained.

In this case, a $ZnFe_2O_4$ catalyst used in the oxidative dehydrogenation reaction of butene is generally produced by a coprecipitation method. In the coprecipitation, the $ZnFe_2O_4$ catalyst is produced by subjecting the raw materials to precipitation, stirring, aging, washing, drying, and firing processes, and a step in which zinc (Zn) and ferrite (Fe) are homogeneously precipitated is very important.

There is a problem in that in the process of synthesizing a zinc ferrite catalyst using the coprecipitation method in the related art, an $\alpha$-$Fe_2O_3$ phase is formed. The $\alpha$-$Fe_2O_3$ phase exhibits a low butadiene selectivity in the oxidative dehydrogenation reaction of butene, whereas the $ZnFe_2O_4$ phase exhibits high butadiene selectivity.

Accordingly, as a result of investigating a synthesis method capable of controlling production of the $\alpha$-$Fe_2O_3$ phase in order to improve the butadiene selectivity, the present inventors found that unlike a method of simultaneously dissolving and precipitating a zinc precursor and a ferrite precursor in a process of synthesizing a zinc ferrite catalyst using an existing coprecipitation method, when the zinc ferrite catalyst is produced by a process of synthesizing the catalyst by first precipitating the zinc precursor then the ferrite precursor, the $\alpha$-$Fe_2O_3$ phase is reduced and the activity of the catalyst is increased, and as a result, 1,3-butadiene could be ultimately obtained at high yield by increasing the selectivity of butadiene in the oxidative dehydrogenation reaction of butene.

According to an exemplary embodiment of the present specification, the preparing of the zinc precursor solution can dissolve a zinc precursor in an amount of 0.1 part by weight to 99 parts by weight based on 100 parts by weight of deionized water (DI water) in the deionized water. Specifically, the amount can be 1 part by weight to 99 parts by weight based on 100 parts by weight of the deionized water. Specifically, it is preferred that the amount is 1 part by weight to 97 parts by weight based on 100 parts by weight of the deionized water.

When the amount of the zinc precursor satisfies the above range, a zinc ferrite catalyst is easily synthesized according to the precipitation order.

According to an exemplary embodiment of the present specification, the preparing of the ferrite precursor solution can dissolve a ferrite precursor in an amount of 1 part by weight to 80 parts by weight based on 100 parts by weight of deionized water (DI water) in the deionized water. Specifically, the amount can be 3 parts by weight to 80 parts by weight based on 100 parts by weight of the deionized water. Specifically, it is preferred that the amount is 5 parts by weight to 70 parts by weight based on 100 parts by weight of the deionized water.

When the amount of the ferrite precursor satisfies the above range, a zinc ferrite catalyst is easily synthesized according to the precipitation order.

According to an exemplary embodiment of the present specification, the zinc precursor and the ferrite precursor can be each independently one or more salts selected from the group consisting of nitrate, ammonium salt, sulfate, and chloride, or a hydrate thereof. Specifically, it is preferred that the zinc precursor and the ferrite precursor are each independently nitrate or chloride, or a hydrate thereof.

According to an exemplary embodiment of the present specification, the zinc precursor can be zinc chloride ($ZnCl_2$). In this case, the formation of the zinc ferrite catalyst is excellent.

According to an exemplary embodiment of the present specification, the ferrite precursor can be ferric chloride hydrate ($FeCl_3 \cdot 6H_2O$). In this case, the formation of the zinc ferrite catalyst is excellent.

According to an exemplary embodiment of the present specification, the deionized water (DI water) can be at a temperature more than 0° C. and 40° C. or less. Preferably, DI water can be at a temperature more than 0° C. and 30° C. or less. More preferably, the DI water can be at a temperature more than 5° C. and 25° C. or less. When the temperature of the deionized water satisfies the above range, the selectivity and yield of butadiene according to the oxidative dehydrogenation reaction can be ultimately improved by increasing the amount of catalyst produced by the precipitation and adjusting the content of the active catalyst According to an exemplary embodiment of the present specification, a pH of the aqueous basic solution can be 7 to 10. Preferably, the pH can be 7.5 to 9. When the pH satisfies the above range, there is an effect of stably producing the zinc ferrite catalyst.

According to an exemplary embodiment of the present specification, the aqueous basic solution can comprise one or more bases selected from the group consisting of potassium hydroxide, ammonium carbonate, ammonium bicarbonate, sodium hydroxide, sodium carbonate, and ammonium hydroxide. Preferably, the aqueous basic solution can be ammonia water. In this case, in the production process of synthesizing a zinc ferrite catalyst by varying the precipitation order, there is an effect that facilitates precipitation, and thus makes the formation of catalyst particles excellent.

According to an exemplary embodiment of the present specification, a concentration of the aqueous basic solution can be 5 wt % to 20 wt %. Preferably, the concentration can be 5 wt % to 10 wt %.

According to an exemplary embodiment of the present specification, the filtering of the second precipitate is not particularly limited as long as the method is a filtration method typically used in the art. For example, the method can be vacuum filtration. Specifically, the method can be a method of filtering the second precipitate by using a vacuum pump to reduce pressure, and in this case, there is an effect that separates the catalyst from washing liquid and moisture.

According to an exemplary embodiment of the present specification, the drying of the second precipitate is not particularly limited as long as the method is a drying method typically used in the art. For example, a dryer can be used, and an oven can be used.

According to an exemplary embodiment of the present specification, the drying of the second precipitate can be performed in an oven at 70° C. to 100° C. Preferably, the second precipitate can be dried in an oven at 80° C. to 100° C.

According to an exemplary embodiment of the present specification, the firing of the second precipitate can increase an initial temperature of 80° C. at a rate of 1° C./min and maintaining the temperature at 600° C. to 800° C. for 5 hours to 10 hours. In the firing of the second precipitate, the second precipitate can be fired specifically at 600° C. to 700° C., and more specifically at 600° C. to 650° C. In the firing of the second precipitate, the second precipitate can be fired specifically for 5 hours to 8 hours, and more specifically for 5 hours to 6 hours.

According to the above temperature range, the crystal size of the $ZnFe_2O_4$ structure of the catalyst is controlled, and the size of the crystals tends to increase as the temperature is increased. In the dehydrogenation reaction of the present application, the adsorption and desorption of oxygen are very important, and the higher the crystallinity is, the less oxygen is desorbed, so that the reactivity can be decreased. For example, a commercially available $ZnFe_2O_4$ catalyst exhibits very good crystallinity, but the activity is very low in the present reaction. For this reason, it is very important to produce a catalyst having appropriate crystallinity, and it can be said that the firing temperature is essential for the catalyst.

It is generally known that the above time range has a tendency similar to temperature, but the time range can be less effective than increasing the temperature, and if the time is maintained too long, the production time is too long when several tons of catalyst is later produced in the commercialization step time, so that the firing time is generally adjusted to 6 hours or so in the laboratory setting.

Accordingly, the firing of the second precipitate according to an exemplary embodiment of the present application can control the crystal size of the zinc ferrite catalyst by increasing an initial temperature at 80° C. at a rate of 1° C./min and maintaining the temperature at 600° C. to 800° C. for 5 hours to 10 hours. When the temperature and the time are out of the above temperature and time ranges, if the temperature is much less than 600° C., crystals are weakly formed, so that the stability structurally deteriorates. In contrast, when the temperature is more than 800° C., the crystallinity is so high that a less active catalyst can be rather produced. In conclusion, appropriate crystallinity is important in consideration of characteristics and reaction characteristics of the feed, and can be controlled by temperature and time in the firing of the second precipitate.

The firing method can be a heat treatment method typically used in the art.

Further, an exemplary embodiment of the present specification provides a zinc ferrite catalyst produced by the above-described method for producing a zinc ferrite catalyst.

According to an exemplary embodiment of the present specification, in the zinc ferrite catalyst produced by the above-described method for producing a zinc ferrite catalyst, a molar ratio (ferrite/zinc ($Fe/Zn^a$)) of ferrite to zinc can be 1 to 2.5. Preferably, the molar ratio can be 2 to 2.5. More preferably, the molar ratio can be 2 to 2.4. When the molar ratio of ferrite to zinc is within the above range, the molar ratio is helpful in increasing the crystal structure and activity of the zinc ferrite catalyst and the zinc ferrite phase is excellently formed by adjusting the $\alpha$-$Fe_2O_3$ phase within a certain range, so that there is an effect in that the selectivity and yield of butadiene according to the oxidative dehydrogenation reaction are excellent.

In the present specification, the molar ratio (ferrite/zinc ($Fe/Zn^a$)) of ferrite to zinc is a value measured to see to what degree the ratio of Fe/Zn on the surface of an actual catalyst measured through an energy dispersive X-ray spectrometer (EDS) characteristic analysis is dispersed.

Another exemplary embodiment of the present specification provides a zinc ferrite catalyst in which a molar ratio (ferrite/zinc ($Fe/Zn^a$)) of ferrite to zinc is 1 to 2.5.

According to an exemplary embodiment of the present specification, the molar ratio (Fe/Zn) of ferrite to zinc of the zinc ferrite catalyst can be 1 to 2.5, preferably 2 to 2.5. More preferably, the molar ratio can be 2 to 2.4. When the molar ratio of ferrite to zinc satisfies the above range, the zinc ferrite phase is predominantly formed by adjusting the $\alpha$-$Fe_2O_3$ phase within a certain range, so that there is an effect in that the selectivity and yield of butadiene according to the oxidative dehydrogenation reaction are excellent.

Further, an exemplary embodiment of the present specification provides a method for producing butadiene, the method comprising: preparing the above-described zinc ferrite catalyst; and producing butadiene by using the zinc ferrite catalyst in an oxidative dehydrogenation reaction of butene.

According to an exemplary embodiment of the present specification, the producing of the butadiene can allow a raw material comprising C4 oil components, steam, oxygen ($O_2$), and nitrogen ($N_2$) to react under the conditions of a reaction temperature of 400° C. to 600° C., a pressure condition of 0.1 bar to 10 bar, and a gas hourly space velocity (GHSV) of 200 $h^{-1}$ to 400 $h^{-1}$.

The C4 oil component can mean C4 raffinate-1,2,3 remaining by separating useful compounds from a C4 mixture produced by a naphtha cracking process, and can mean C4 classes which can be obtained through ethylene dimerization.

According to an exemplary embodiment of the present specification, the C4 oil component can be one or a mixture of two or more selected from the group consisting of n-butane, trans-2-butene, cis-2-butene, and 1-butene.

According to an exemplary embodiment of the present specification, the steam or nitrogen ($N_2$) is a diluted gas introduced for the purpose of reducing the explosion danger of the reactant, simultaneously preventing coking of the catalyst, removing the reaction heat, and the like in the oxidative dehydrogenation reaction.

According to an exemplary embodiment of the present specification, the oxygen ($O_2$) is an oxidant and reacts with C4 oil components to cause a dehydrogenation reaction.

According to an exemplary embodiment of the present specification, the oxidative dehydrogenation reaction can proceed according to the following Reaction Formula 1 or Reaction Formula 2.

$$C_4H_8 + \tfrac{1}{2}O_2 \rightarrow C_4H_6 + H_2O \quad \text{[Reaction Formula 1]}$$

$$C_4H_{10} + O_2 \rightarrow C_4H_6 + 2H_2O \quad \text{[Reaction Formula 2]}$$

Hydrogen of butane or butene is removed from the oxidative dehydrogenation reaction, and as a result, butadiene is produced. Meanwhile, the oxidative dehydrogenation reaction can produce a side reaction product comprising carbon monoxide (CO), carbon dioxide ($CO_2$), or the like except for the main reaction such as Reaction Formula 1 or 2. The oxidative dehydrogenation reaction can comprise a process in which the side reaction product is separated so as not to be continuously accumulated in the process, and is released out of the system.

According to an exemplary embodiment of the present specification, in the method for producing butadiene, the conversion of butene can be 72% or more, preferably 72.5% or more, and more preferably 79% or more.

According to an exemplary embodiment of the present specification, in the method for producing butadiene, the selectivity of butadiene can be 85% or more, preferably 85.8% or more, and more preferably 87% or more.

Figure 1:
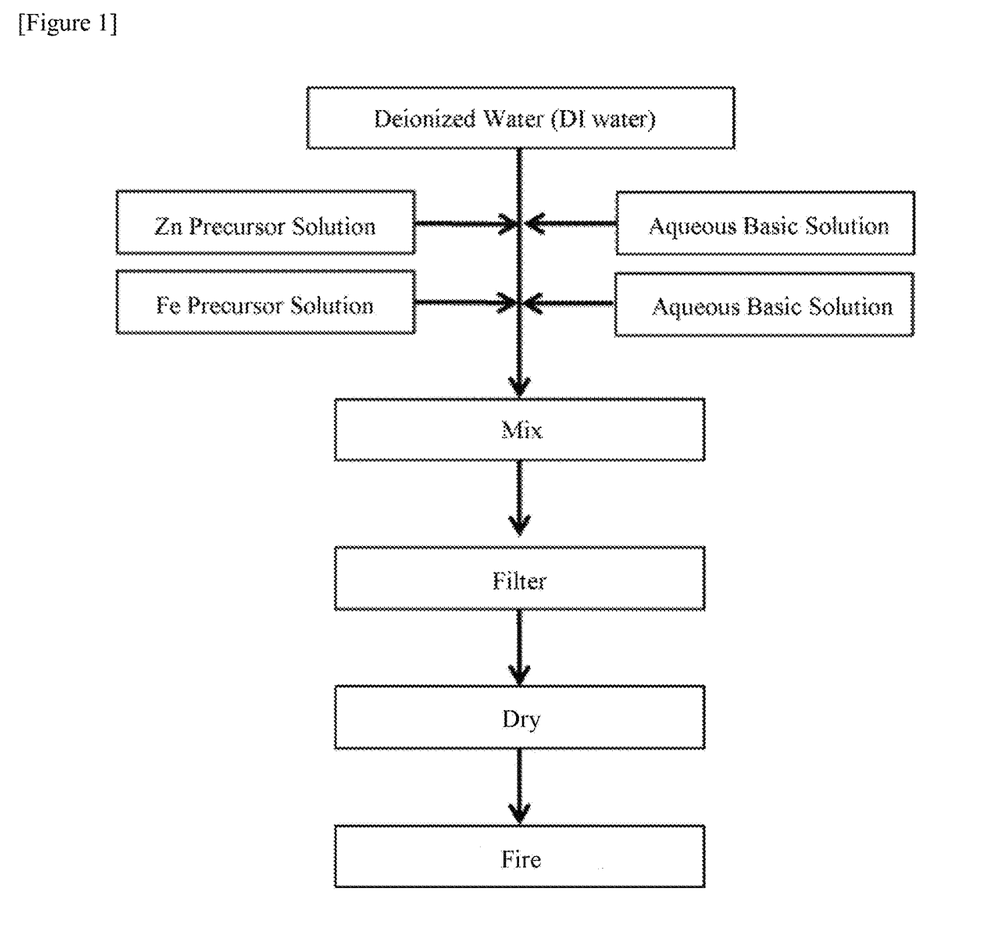
FIG. 1 is a process diagram for performing a method for producing a zinc ferrite catalyst according to an exemplary embodiment of the present specification.
Figure 2:
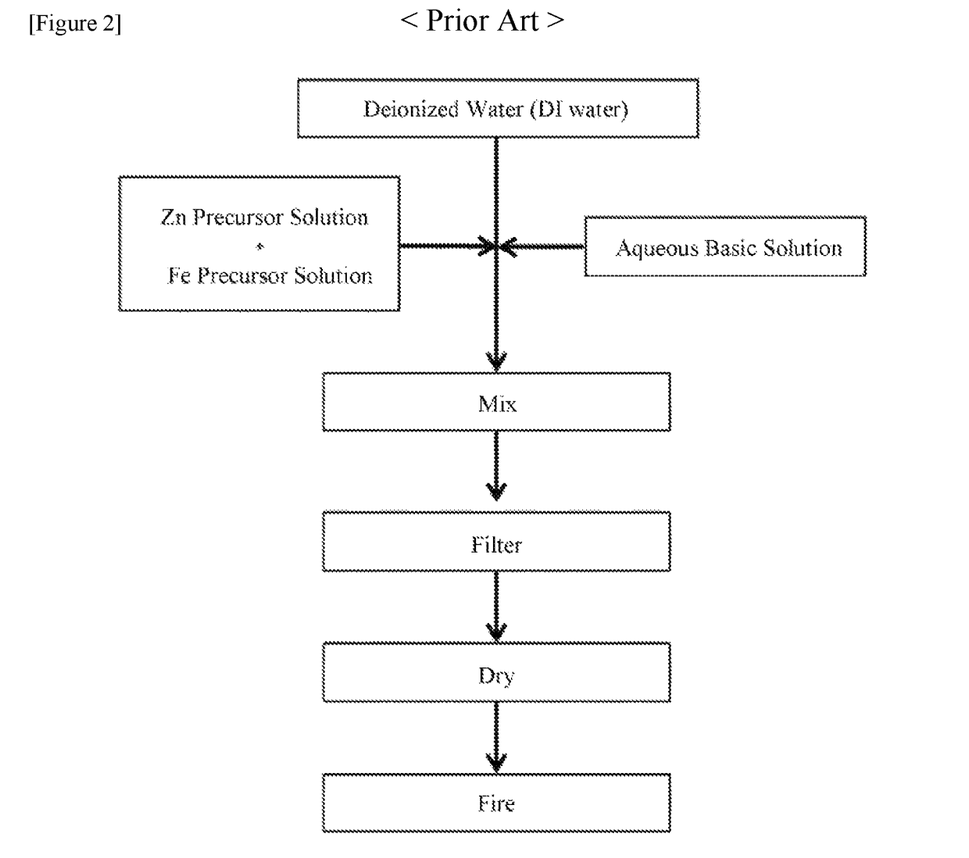
FIG. 2 is a process diagram for performing a method for producing a zinc ferrite catalyst according to a coprecipitation method in the related art.

FIG. 1 is an exemplary process diagram for performing a method for producing a zinc ferrite catalyst according to an exemplary embodiment of the present specification.

According to FIG. 1, in a coprecipitation method of a zinc ferrite catalyst, the zinc ferrite catalyst can be synthesized by adjusting the precipitation order of the zinc precursor and the ferrite precursor. In particular, in the case where the zinc ferrite catalyst is synthesized by first precipitating the zinc precursor then the ferrite precursor, the α-$Fe_2O_3$ phase is decreased and the activity of the catalyst is increased, unlike the existing method of simultaneously dissolving and coprecipitating the zinc precursor and the ferrite precursor.

As described above, according to an exemplary embodiment of the present specification, during the process of producing an advantageous zinc ferrite catalyst as a catalyst for the oxidative dehydrogenation reaction of butene, when the zinc ferrite catalyst is synthesized by varying the precipitation order of the zinc precursor and the ferrite precursor, butadiene can be ultimately produced at high yield by increasing the conversion of butene and the selectivity of butadiene.

MODE FOR INVENTION

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

Example 1

A Fe precursor solution was prepared by dissolving 47.667 g of $FeCl_3 \cdot 6H_2O$ as a Fe precursor in 710.2 g of deionized water (DI water). A Zn precursor solution was prepared by dissolving 2.019 g of $ZnCl_3$ as a Zn precursor in 125.3 g of deionized water (DI water).

The pH was adjusted to 9 by simultaneously dropping the Zn precursor solution and 9 wt % of ammonia water in 8,500 g of DI water at 15° C. for precipitation using a circulator, and subsequently, the Fe precursor solution and 9 wt % of ammonia water were simultaneously dropped in DI water in which the Zn precursor solution was precipitated for precipitation.

A formed catalyst compound was subjected to a filtering process, and then dried in an oven at 90° C., and a zinc ferrite catalyst was obtained by performing firing (calcination) at an air atmosphere (1 L/min). For the firing, the temperature was increased at 80° C. and 1° C./min, and was maintained at 650° C. for 6 hours.

Example 2

A Fe precursor solution was prepared by dissolving 1,132.219 g of $FeCl_3 \cdot 6H_2O$ as a Fe precursor in 1,700 g of deionized water (DI water). A Zn precursor solution was prepared by dissolving 288.456 g of $ZnCl_3$ as a Zn precursor in 300 g of DI water.

The pH was adjusted to 7.5 by simultaneously dropping the Zn precursor solution and 9 wt % of ammonia water in 2,000 g of DI water at 15° C. for precipitation using a circulator, and subsequently, the Fe precursor solution and ammonia water were together dropped in DI water in which the Zn precursor solution was precipitated for precipitation.

A formed catalyst compound was subjected to a filtering process, and then dried in an oven at 90° C., and a zinc ferrite catalyst was obtained by performing firing (calcination) at an air atmosphere (1 L/min). For the firing, the temperature was increased at 80° C. and 1° C./min, and was maintained at 650° C. for 6 hours.

Comparative Example 1

A zinc ferrite catalyst was synthesized in the same manner as in Example 1, except the pH was adjusted to 9 by simultaneously dropping the Fe precursor solution and ammonia water in 8,500 g of deionized water (DI water) for precipitation, and subsequently, the Zn precursor solution and ammonia water were simultaneously dropped in DI water in which the Fe precursor solution was precipitated for precipitation.

Comparative Example 2

The pH was adjusted to 9 by dropping a precursor solution in which 47.667 g of $FeCl_3 \cdot 6H_2O$ as a Fe precursor and 2.019 g of $ZnCl_3$ as a Zn precursor were dissolved in 835.5 g of deionized water (DI water) and 9 wt % of ammonia water in 8,500 g of deionized water (DI water) at 15° C. using a circulator, thereby synthesizing a catalyst.

A formed catalyst compound was subjected to a filtering process, and then dried in an oven at 90° C., and a zinc ferrite catalyst was obtained by performing firing (calcination) at an air atmosphere (1 L/min). For the firing, the temperature was increased at 80° C. and 1° C./min, and was maintained at 650° C. for 6 hours.

Comparative Example 3

The pH was adjusted to 7.5 by simultaneously dropping a precursor solution in which 1,132.219 g of $FeCl_3 \cdot 6H_2O$ as a Fe precursor and 288.456 g of $ZnCl_3$ as a Zn precursor were dissolved in 2,000 g of deionized water (DI water) and 9 wt % of ammonia water in 2,000 g of DI water at 15° C. using a circulator, thereby synthesizing a catalyst.

A formed catalyst compound was subjected to a filtering process, and then dried in an oven at 90° C., and a zinc ferrite catalyst was obtained by performing firing (calcination) at an air atmosphere (1 L/min). For the firing, the temperature was increased at 80° C. and 1° C./min, and was maintained at 650° C. for 6 hours.

Comparative Example 4

A zinc ferrite catalyst was synthesized in the same manner as in Comparative Example 3, except that the pH was adjusted to 8.0.

Comparative Example 5

A zinc ferrite catalyst was synthesized in the same manner as in Comparative Example 3, except that the pH was adjusted to 8.5.

Figure 3:
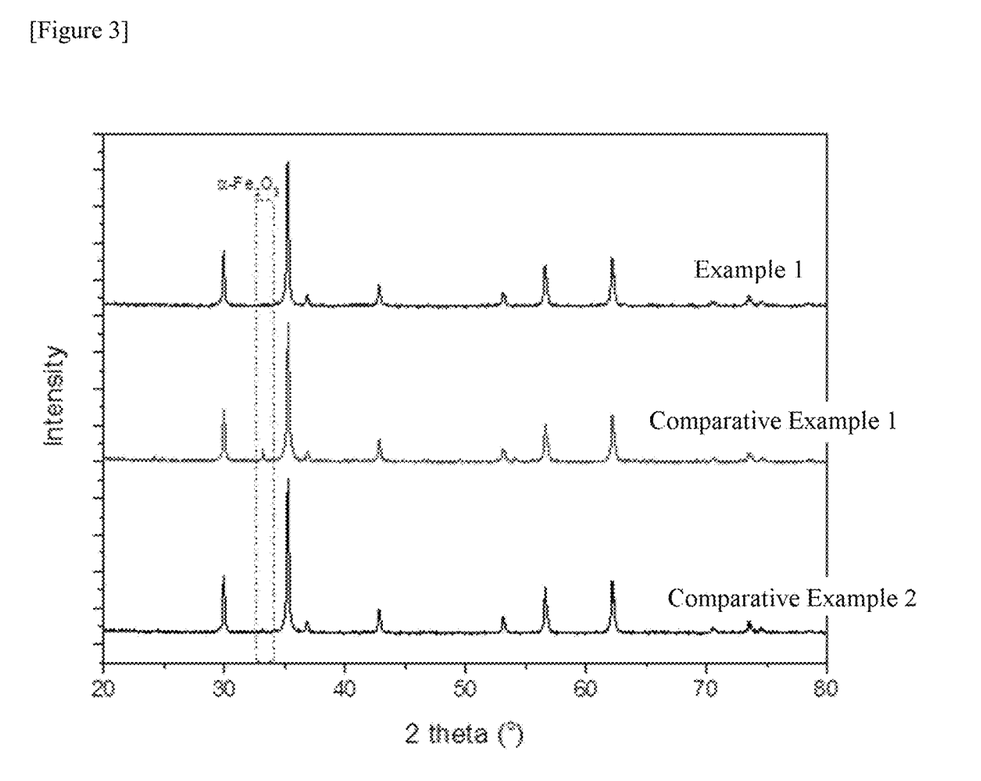
FIG. 3 is a view illustrating results of measuring the intensity of the zinc ferrite catalysts produced according to Example 1 and Comparative Examples 1 and 2 of the present specification.

The results of measuring the intensity of the zinc ferrite catalysts produced according to Example 1 and Comparative Examples 1 and 2 are illustrated in FIG. 3.

Figure 4:
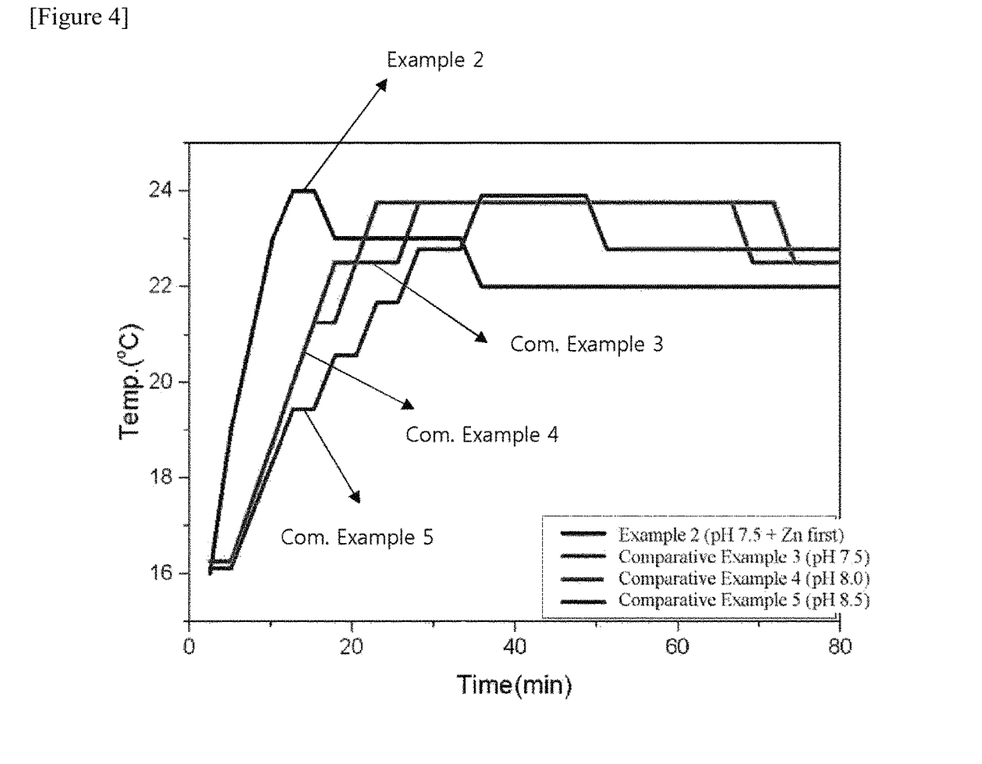
FIG. 4 is a view illustrating results of measuring the change in temperature over time of the zinc ferrite catalysts produced according to Example 2 and Comparative Examples 3 to 5 of the present specification.

The results of measuring the change in temperature over time of the zinc ferrite catalysts produced according to Example 2 and Comparative Examples 3 to 5 are illustrated in FIG. 4.

Figure 5:
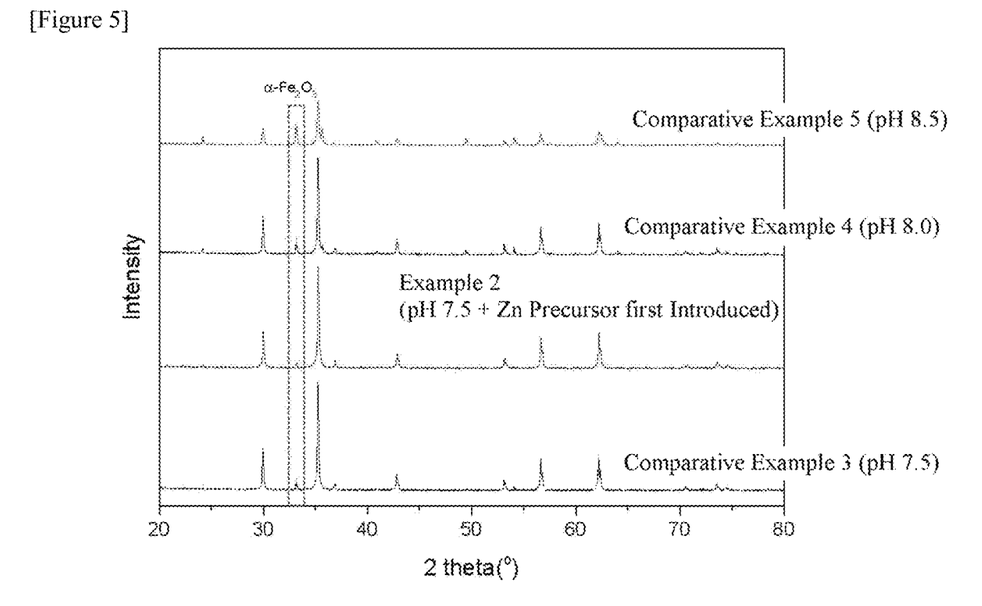
FIG. 5 is a view illustrating results of measuring the intensity of the zinc ferrite catalysts produced according to Example 2 and Comparative Examples 3 to 5 of the present specification.

The results of measuring the intensity of the zinc ferrite catalysts produced according to Example 2 and Comparative Examples 3 to 5 are illustrated in FIG. 5.

According to FIG. 3, it can be seen that in the case of the zinc ferrite catalyst in Comparative Example 2 synthesized by simultaneously coprecipitating the Zn precursor and the Fe precursor, the $\alpha$-$Fe_2O_3$ phase is observed.

Further, it can be confirmed that in the case of the zinc ferrite catalyst in Comparative Example 1 synthesized by first introducing the Fe precursor, and subsequently precipitating the Zn precursor, the $\alpha$-$Fe_2O_3$ phase is detected more than in the case of the zinc ferrite catalyst in Comparative Example 2 produced according to the related art.

Meanwhile, according to FIG. 3, it can be confirmed that in the case of the zinc ferrite catalyst in Example 1 synthesized by first introducing the Zn precursor, and subsequently precipitating the Fe precursor, the $\alpha$-$Fe_2O_3$ phase is not observed.

According to FIG. 4, it can be confirmed that when the temperature of the coprecipitation bath is adjusted to 15° C., the temperature of the coprecipitation solution exhibits a temperature of 17° C. in the early stage, and when the coprecipitation begins, the temperature of the precipitation solution tends to be slowly increased up to 24° C. by neutralization heat.

In the case of Example 2, at the moment when the coprecipitation begins, the temperature reaches 24° C., and then the temperature is decreased, so that the reaction heat is easily controlled.

According to FIG. 5, it can be confirmed that in the case of a concentrated catalyst, the zinc ferrite catalysts in Comparative Examples 3 to 5 synthesized by simultaneously coprecipitating the Zn precursor and the Fe precursor exhibit the lowest $\alpha$-$Fe_2O_3$ phase in Comparative Example 3 where the pH is 7.5, and a level of 2.47 is observed as a result of EDS.

Meanwhile, according to FIG. 5, it can be confirmed that the zinc ferrite catalyst in Example 2 synthesized by first introducing the Zn precursor, and subsequently precipitating the Fe precursor exhibits a lower $\alpha$-$Fe_2O_3$ phase than in Comparative Example 3, and a level of 2.33 is observed as a result of EDS.

Consequently, according to Examples 1 and 2 and Comparative Examples 1 to 5, it can be seen that as the zinc ferrite catalysts are concentrated, the $\alpha$-$Fe_2O_3$ phase is increased, and in this case, as in Example 2, it can be confirmed that the precipitation method of first introducing the Zn precursor is helpful in increasing the activity of the catalyst by adjusting the crystal structure and $\alpha$-$Fe_2O_3$ phase of the catalyst.

Experimental Example 1

Under the conditions of 400° C., GHSV=250 $h^{-1}$, OBR=1, SBR=5, and NBR=4, 1,3-butadiene was produced from the oxidative dehydrogenation reaction by using the zinc ferrite catalyst produced in Example 1.

Experimental Example 2

1,3-butadiene was produced in the same manner as in Experimental Example 1, except that in Experimental Example 1, the temperature was 440° C.

Comparative Example 6

Under the conditions of 400° C., GHSV=250 $h^{-1}$, OBR=1, SBR=5, and NBR=4, 1,3-butadiene was produced from the oxidative dehydrogenation reaction by using the zinc ferrite catalyst produced in Comparative Example 1.

Comparative Example 7

1,3-butadiene was produced in the same manner as in Comparative Example 6, except that in Comparative Example 6, the temperature was 440° C.

Comparative Example 8

Under the conditions of 400° C., GHSV=250 $h^{-1}$, OBR=1, SBR=5, and NBR=4, 1,3-butadiene was produced from the oxidative dehydrogenation reaction by using the zinc ferrite catalyst produced in Comparative Example 2.

Comparative Example 9

1,3-butadiene was produced in the same manner as in Comparative Example 8, except that in Comparative Example 8, the temperature was 440° C.

(OBR=Oxygen/total 2-butene ratio
SBR=Steam/total 2-butene ratio
NBR=Nitrogen/total 2-butene ratio)

As a result of analyzing Fe/$Zn^a$ by EDS in Experimental Examples 1 and 2 and Comparative Examples 6 to 9, the results of calculating the conversion of butene and the selectivity of butadiene by using GC devices are shown in the following Table 1.

TABLE 1

| Classification | Precursor introduction order | Fe/Zn$^a$ (mol ratio) | Reaction temperature | Butene conversion (%) | Butadiene selectivity (%) |
|---|---|---|---|---|---|
| Experimental Example 1 | 1. Zn, 2. Fe (Example 1) | 2.39 | 400° C. | 79.1 | 87.9 |
| Experimental Example 2 | | | 400° C. | 72.5 | 86.8 |
| Comparative Example 6 | 1. Fe, 2. Zn (Comparative Example 1) | 2.73 | 400° C. | 66.6 | 82.5 |
| Comparative Example 7 | | | 440° C. | 70.4 | 83.8 |
| Comparative Example 8 | Zn + Fe (Comparative Example 2) | 2.66 | 400° C. | 74.7 | 86.7 |
| Comparative Example 9 | | | 440° C. | 70.4 | 86.1 |

(Fe/Zn$^a$: Estimated from EDS)

According to Table 1, it could be confirmed that in the case of the zinc ferrite catalyst in Example 1 synthesized by first introducing the Zn precursor then the Fe precursor as in Experimental Examples 1 and 2, the Fe/Zn$^a$ ratio was at a level of 2.39, the zinc ferrite catalyst was synthesized at a level lower than 2.66 which is a Fe/Zn$^a$ ratio of the zinc ferrite catalysts in Comparative Examples 8 and 9 synthesized by the related art.

When Experimental Examples 1 and 2 are compared with Comparative Examples 6 and 7, it could be confirmed that in the case of Experimental Examples 1 and 2 in which the catalyst was synthesized by first introducing the Zn precursor, and subsequently precipitating the Fe precursor, under the reaction conditions of 400° C. and 440° C., both the butene conversion and the butadiene selectivity are better than those in the case of Comparative Examples 6 and 7 in which the catalyst was synthesized by first introducing the Fe precursor, and subsequently precipitating the Zn precursor.

Further, when Experimental Examples 1 and 2 are compared with Comparative Examples 8 and 9, it could be confirmed that in the case of Experimental Examples 1 and 2 in which the catalyst was synthesized by first introducing the Zn precursor, and subsequently precipitating the Fe precursor, under the reaction conditions of 400° C. and 440° C., both the butene conversion and the butadiene selectivity are better than those in the case of Comparative Examples 8 and 9 in which the catalyst was synthesized by simultaneously coprecipitating the Zn precursor and the Fe precursor.

As confirmed in FIG. 3, it could be confirmed that this is because the $\alpha$-Fe$_2$O$_3$ phase was not observed in the case of the zinc ferrite catalyst in Example 1 synthesized by first introducing the Zn precursor, and subsequently precipitating the Fe precursor.

The $\alpha$-Fe$_2$O$_3$ phase exhibits low butadiene selectivity in the oxidative dehydrogenation reaction of butene, and in the case of the zinc ferrite catalyst in Comparative Example 2 synthesized by simultaneously precipitating the Zn precursor and the Fe precursor and the zinc ferrite catalyst in Comparative Example 1 synthesized by first introducing the Fe precursor, and subsequently precipitating the Zn precursor, the $\alpha$-Fe$_2$O$_3$ phase was observed, so that for this reason, the conversion of butene and the selectivity of butadiene have low values as compared to the zinc ferrite catalyst in Example 1 according to the present invention, meaning that the activity of the catalyst was decreased.

Consequently, it could be confirmed that in the process of producing a zinc ferrite catalyst through a coprecipitation method, the precipitation method of first introducing the Zn precursor and then introducing the Fe precursor was helpful in increasing the crystal structure and activity of the catalyst.

Experimental Example 3

For the zinc ferrite catalyst produced in Example 2, the results of measuring the weight and Fe/Zn$^a$ ratio of ZnFe$_2$O$_4$ and $\alpha$-Fe$_2$O$_3$ by using an X-ray diffraction (XRD) analysis method are shown in the following Table 2.

Comparative Examples 10 to 12

For each of the zinc ferrite catalysts produced in Comparative Examples 3 to 5, the results of measuring the weight and Fe/Zn$^a$ ratio of ZnFe$_2$O$_4$ and $\alpha$-Fe$_2$O$_3$ by using an X-ray diffraction (XRD) analysis method are shown in the following Table 2.

TABLE 2

| Classification | Precursor introduction order | XRD ZnFe$_2$O$_4$ (wt %) | $\alpha$-Fe$_2$O$_3$ (wt %) | Fe/Zn$^a$ |
|---|---|---|---|---|
| Experimental Example 3 | 1. Zn, 2. Fe (Example 2) | 95.72 | 4.28 | 2.33 |
| Comparative Example 10 | Zn + Fe (Comparative Example 3) | 93.62 | 6.38 | 2.47 |
| Comparative Example 11 | Zn + Fe (Comparative Example 4) | 86.25 | 13.75 | 2.95 |
| Comparative Example 12 | Zn + Fe (Comparative Example 5) | 61.58 | 38.42 | 4.55 |

According to Table 2, it could be confirmed that in the case of the zinc ferrite catalyst in Example 2 synthesized by first introducing the Zn precursor and then introducing the Fe precursor as in Experimental Example 3, the Fe/Zn$^a$ ratio was at a level of 2.33, and the zinc ferrite catalyst was synthesized at a level lower than 2.47 which is a Fe/Zn$^a$ ratio of the zinc ferrite catalyst in Comparative Example 10.

In addition, in the case of the weight of ZnFe$_2$O$_4$ and $\alpha$-Fe$_2$O$_3$ measured according to the XRD analysis method, it could be confirmed that in Experimental Example 3, the weight of $\alpha$-Fe$_2$O$_3$ was 4.28 wt %, which was the lowest level detected.

Consequently, in the process of producing the zinc ferrite catalyst through the coprecipitation method, it could be confirmed that the precipitation method of first introducing the Zn precursor, and then introducing the Fe precursor was helpful in controlling the $\alpha$-Fe$_2$O$_3$ phase when synthesizing a concentrated catalyst.

Although the preferred exemplary embodiments of the present invention have been described above, the present invention is not limited thereto, and various modifications can be made and carried out within the scope of the claims and the detailed description of the invention, and also fall within the scope of the invention.

The invention claimed is:

1. A method for producing a zinc ferrite catalyst, the method comprising:
   preparing a zinc precursor solution;
   preparing a ferrite precursor solution;
   obtaining a first precipitate by bringing the zinc precursor solution into contact with an aqueous basic solution by simultaneously dropping the zinc precursor solution and the aqueous basic solution having a pH of 7 to 10 into deionized water at a temperature of more than 5° C. and 15° C. or less;

obtaining a second precipitate by adding the ferrite precursor solution to the first precipitate; and drying and firing the second precipitate after filtering the second precipitate.

2. The method of claim 1, wherein the preparing of the zinc precursor solution comprises dissolving a zinc precursor in an amount of 0.1 part by weight to 99 parts by weight based on 100 parts by weight of deionized water (DI water) in the DI water.

3. The method of claim 1, wherein the preparing of the ferrite precursor solution comprises dissolving a ferrite precursor in an amount of 1 part by weight to 80 parts by weight based on 100 parts by weight of deionized water (DI water) in the DI water.

4. The method of claim 1, wherein the zinc precursor and the ferrite precursor are each independently one or more salts selected from the group consisting of nitrate, ammonium salt, sulfate, and chloride, or a hydrate thereof.

5. The method of claim 1, wherein the zinc precursor is zinc chloride ($ZnCl_2$).

6. The method of claim 1, wherein the ferrite precursor is ferric chloride hydrate ($FeCl_3 \cdot 6H_2O$).

7. The method of claim 1, wherein the aqueous basic solution comprises one or more bases selected from the group consisting of potassium hydroxide, ammonium carbonate, ammonium bicarbonate, sodium hydroxide, sodium carbonate, and ammonium hydroxide.

8. The method of claim 1, wherein the firing of the second precipitate comprises increasing an initial temperature of 80° C. at a rate of 1° C./min and maintaining the temperature at 600° C. to 800° C. for 5 hours to 10 hours.

* * * * *